(12) United States Patent
Petrosian et al.

(10) Patent No.: US 6,391,924 B1
(45) Date of Patent: May 21, 2002

(54) TAURINE DERIVATIVES USEABLE IN THE TREATMENT OF OPHTHALMIC DISORDERS

(75) Inventors: Andranik M. Petrosian; Jasmine E. Haroutounian; Armen Vartanian, all of Yerevan (AM)

(73) Assignee: Hampar Karageozian, San Juan Capistrano, CA (US)

( * ) Notice: Subject to any disclaimer, the term of this patent is extended or adjusted under 35 U.S.C. 154(b) by 0 days.

(21) Appl. No.: 08/982,249

(22) Filed: Dec. 10, 1997

(51) Int. Cl.[7] .............................................. A61K 31/07
(52) U.S. Cl. ...................... 514/725; 514/562; 514/912
(58) Field of Search ................................. 514/562, 912, 514/725

(56) References Cited

PUBLICATIONS

A.M, Functional Neuro Chemistry and Cardiology, pp. 471–475, 1990.*

* cited by examiner

Primary Examiner—Zohreh Fay
(74) Attorney, Agent, or Firm—Robert D. Buyan; Stout, Uxa, Buyan & Mullins, LLP

(57) ABSTRACT

Water soluable taurine derivatives, and methods of synthesizing, formulating, and using such taurine derivatives for treating or protecting the retina of a mammalian eye. The invention includes treatment methods which comprise contacting with the retinal tissue, a therapeutically effective amount of retinyliden tauret (3,7-dimethyl-9-(2,6,6-trimehyl-1-cyclohexen-1-yl)-2,4,6,8-nonatetraen-1-imido-(N-ethane sulfonic acid)). The invention also includes methods for synthesizing two (2) specific isomers of retinyliden tauret, namely (A) all-trans-[3,7-dimethyl-9-(2,6,6-trimethyl-1-cyclohexen-1-yl)-2,4,6,8-nonatetraen-1-imido-(N-ethane sulfonic acid)] and (B) 11-cis-[3,7-dimethyl-9-(2,6,6-trimehyl-1-cyclohexen-1-yl)-2,4,6,8-nonatetraen-1-imido-(N-ethane sulfonic acid)]. Also included are formulations and methods for administering such compounds to the retina of a mammalian eye to treat or prevent the progression of retinopathy.

22 Claims, 2 Drawing Sheets

All-trans Retinal
[3,7-dimethyl-9-(2,6,6-trimethyl-1-cyclohexen-1-yl)-2,4,6,8-nonatetraen-1-al]

$CH_3OH/CH_3ONa$

Molecular Sieve
-5C to -20C
Under dark & argon atmosphere

All-trans Retinyliden Taurine
[3,7-dimethyl-9-(2,6,6-trimethyl-1-cyclohexen-1-yl)-2,4,6,8-nonatetraen-1-imido-(N-ethane sulfonic acid)]

TAURINE DERIVATIVES USEABLE IN THE TREATMENT OF OPHTHALMIC DISORDERS

FIELD OF THE INVENTION

The present invention relates generally to pharmaceutical compounds and methods for medical treatment, and more particularly to the composition, synthesis, formulation and use of certain derivatives of the amino acid taurine, for the treatment of ophthalmic disorders.

BACKGROUND OF THE INVENTION

The retina is a layer of cells which form the inside lining of the back of the mammalian eye. The retina includes certain specialized photoreceptor cells which convert light energy into electrical impulses. These specialized photoreceptor cells of the retina include "rods" which emit impulses corresponding to black and white images and "cones" which emit impulses corresponding to colored images.

A number of diseases and disorders of the retina are characterized or caused by degeneration of the retinal tissue. Examples of these degenerative retinopathies include: retinitis pigmentosa, macular degeneration and diabetic retinopathy. The available medical and surgical treatments for these degenerative retinopathies have been less than perfect, and many patients continue to suffer full or partial losses of vision due to these disorders.

Relatively high concentrations of the amino acid taurine have been identified in the outer segments of retinal photoreceptor cells, and it has been determined that taurine may be released from the retina in response to light stimulation. It has been further determined that high levels af taurine in the retina may protects the outer segments of the photoreceptor cells from light-induced structural damage. A postulated mechanism for this photo-protective effect is that certain taurine derivatives (e.g, metabolites or break-down products which are formed by the retina's natural action on the taurine compound) may facilitate the transport of certain photoprotective compounds related to Vitamin A—known as retinoids—between the pigment epithelium and the photoreceptor cells. In particular, applicant's research has identified a particular taurine derivative known as retinyliden tauret which is naturally present in the retina and pigment epithelium, and which has exhibited some photoprotective effects in in vitro experiments performed on frog retinas. It is postulated that cis and trans isomers of retinyliden tauret may facilitate the transport of retinoids, in opposite directions, through microscopic channels in the outer segments of the retina's photoreceptor cells. Tauret: Further Studies of the Role of Taurine in Retina; Petrosian, A. M, Functional Neurochemistry and Cardiology, pp. 471–475 (Wiley-Liss, 1990)

Given the experimentally demonstrated potential for retinyliden tauret to affect light-induced damage to the retina, it is desirable to devise methods for synthesizing retinyliden tauret in substantial quantities, and to develop therapeutic methods for the administration of exogenous retinyliden tauret to the retina of a human or other mammal to deter or treat degenerative retinopathies or to protect the retina from damage.

SUMMARY OF THE INVENTION

The present invention provides methods for treating or protecting the retina of a mammalian eye or other tissues by contacting with the retinal or other tissue a therapeutically effective amount of a water soluble derivative of taurine and retinoic acid. Suck compound my comprise retinyliden tauret, which facilitates the transport of at least one retinoid between the pigment epithelium and the photoreceptor cells of the epithelium.

Further in accordance with the present invention, there are provided methods for synthesizing all-trans-[3,7-dimethyl-9-(2,6,6-trimehyl-1-cyclohexen-1-yl)-2,4,6,8-nonatetraen-1-imido-(N-ethane sulfonic acid)] and 11-cis-[3,7-dimethyl-9-(2,6,6-trimehyl-1-cyclohexen-1-yl)-2,4,6,8-nonatetraen-1-imido-(N-ethane sulfonic acid)], as well as formulations and methods for administering such compounds to the retina of a mammalian eye to treat or protect the retina.

Further aspects and advantages of the invention will become apparent to persons of skill in the art upon reading and understanding of the detailed descriptions of preferred embodiments set forth herebelow.

DETAILED DESCRIPTION OF PREFERRED EMBODIMENT

Information regarding retinyliden tauret and certain experiments demonstrating that such compound plays a role in the transport of retinoids between the pigment epithelium and the photoreceptor cells of the retina, have been published by applicant and colleagues, within the past year, in *Advances in Experimental Biology,* Vol 403, Chapter 35: A Taurine-Related Endogenous Substance in the Retina and its Role in Vision (December 1996), and the entirety of such prior publication is expressly incorporated herein by reference.

A. Methods for Synthesizing the Desired Isomers of 3,7-dimethyl-9-(2,6,6-trimehyl-1-cyclohexen-1-yl)-2,4,6,8-nonatetraen-1-imido-(N-ethane Sulfonic Acid)

The cis and trans isomers of retinyliden tauret having the formula 3,7-dimethyl-9-(2,6,6-trimehyl-1-cyclohexen-1-yl)-2,4,6,8-nonatetraen-1-imido-(N-ethane sulfonic acid) may be synthesized by reacting selected cis and/or trans isomer(s) of retinal, having the general formula 3,7-dimethyl-9-(2,6,6-trimehyl-1-cyclohexen-1-yl)-2,4,6,8-nonatetraen-1-al), with the amino acid taurine (i.e., 2-aminoethanesulfonic acid) in the presence of sodium methylate (i.e., $CH_3 OH/CH_3 ONa$). Preferably, this reaction is carried out in substantial darkness, in an argon atmosphere, at temperatures in the range of −5 to −20 degrees C.

Figure 1:
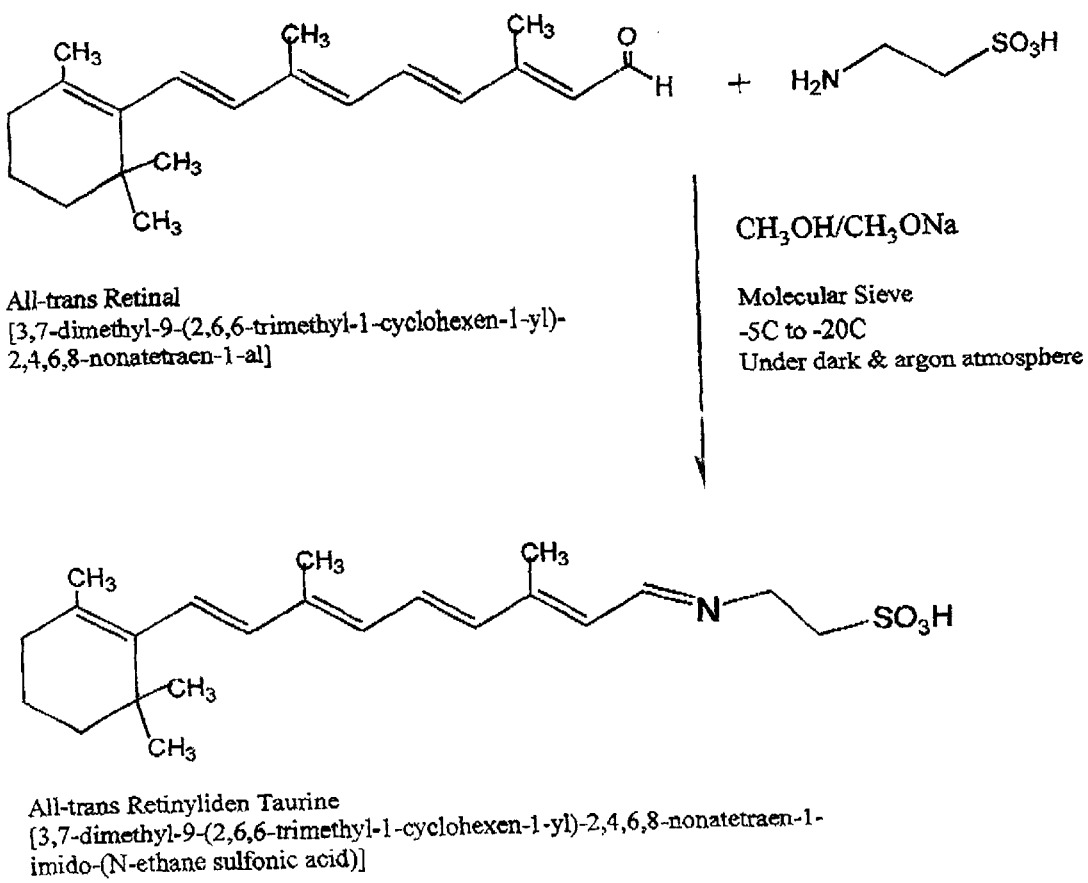
FIG. 1 is a diagram of a preferred method of synthesizing all-trans-[3,7-dimethyl-9-(2,6,6-trimehyl-1-cyclohexen-1-yl)-2,4,6,8-nonatetraen-1-imido-(N-ethane sulfonic acid)].

FIG. 1 shows the the manner in which this synthetic method is used to synthesize the all-trans isomer of retinyliden tauret (i.e., all-trans-3,7-dimethyl-9-(2,6,6-trimehyl-1-cyclohexen-1-yl)-2,4,6,8-nonatetraen-1-imido-(N-ethane sulfonic acid). As shown, this isomer-specific synthesis utilizes all-trans-retinal (i.e., all-trans-3,7-dimethyl-9-(2,6,6-trimehyl-1-cyclohexen-1-yl)-2,4,6,8-nonatetraen-1-al) as a starting material.

Figure 2:
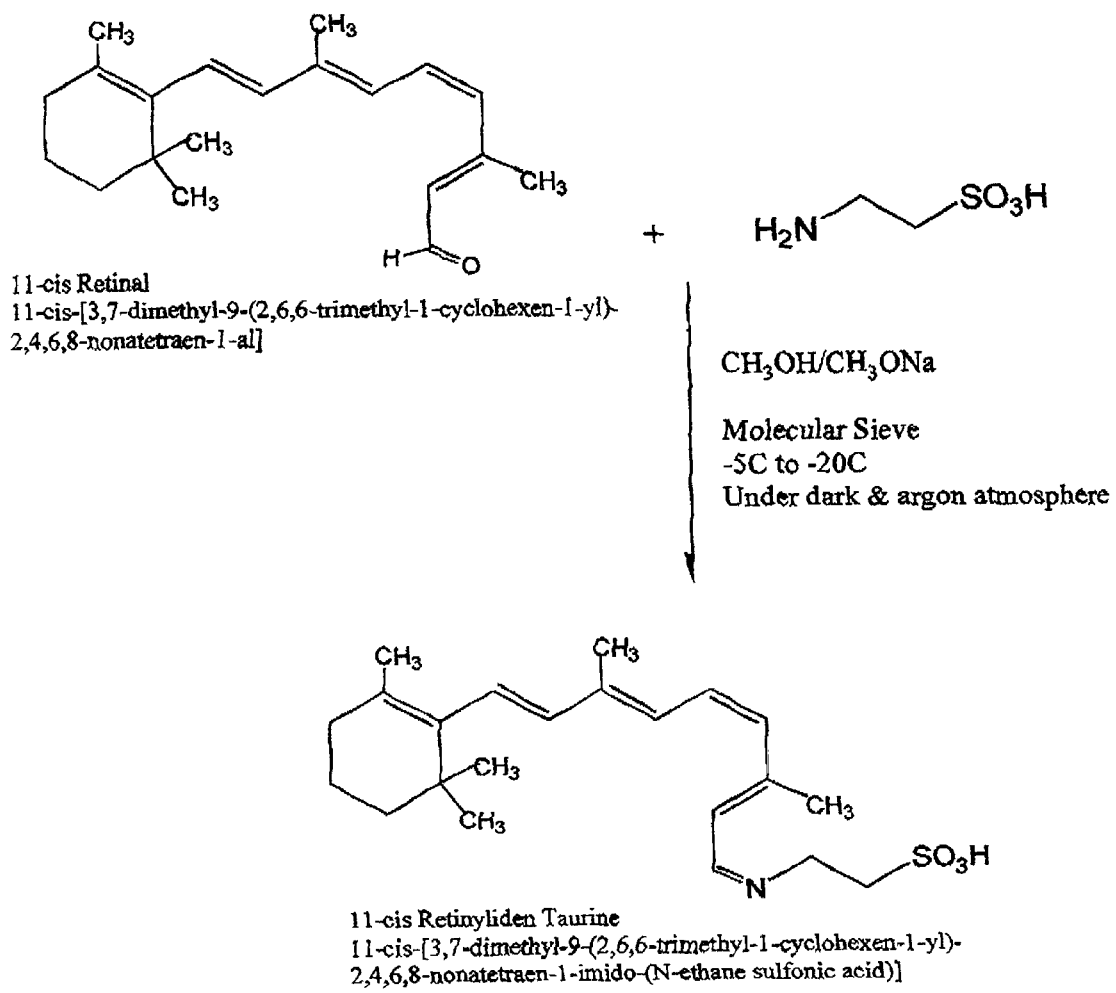
FIG. 2 is a diagram of a preferred method of synthesizing 11-cis-[3,7-dimethyl-9-(2,6,6-trimehyl-1-cyclohexen-1-yl)-2,4,6,8-nonatetraen-1-imido-(N-ethane sulfonic acid)].

FIG. 2 shows the the manner in which this synthetic method is used to synthesize the 11-cis isomer of retinyliden tauret (i.e., 11-cis-3,7-dimethyl-9-(2,6,6-trimehyl-1-cyclohexen-1-yl)-2,4,6,8-nonatetraen-1-imido-(N-ethane sulfonic acid). As shown, this isomer-specific synthesis utilizes 11-cis-retinal (i.e., 11-cis-3,7-dimehyl-9-(2,6,6-trimehyl-1-cyclohexen-1-yl)-2,4,6,8-nonatetraen-1-al) as a starting material.

The particular solvents used, and the conditions under which the reactions proceed, may vary somewhat. However, typically it will be necessary for the reaction to be carried out in the absence of substantial light (e.g., in darkness or under dim red light) at tempratures below 30 degrees C. Set forth in subsections i. and ii. herebelow, are examples of specific synthetic methods for synthesizing all-trans-retinyliden tauret and 11-cis-retinyliden tauret, including particular solvents which may be utilized and the particular conditions under which these reactions may be run.

i. A Preferred Synthesis of All-trans-Retinyliden Tauret

1. Dissolve 60 mg Taurine (i.e., 2-aminoethanesulfonic acid) in 5.0 ml of dehydrated methanol.

2. To the taurine/methanol solution prepared in step 1, add 2.0 ml of 0.8 N Sodium Methylate (i.e., sodium methoxide) in dehydrated methanol.

3. Dissolve 150 mg of all all-trans-retinal (i.e., Vitamin A Aldehyde/Reffnaldehyde or 3,7-dimethyl-9-(2,6,6-trimethyl-1-cyclohexen-1-yl)-2,4,6,8-nonatetraen-1-al) in 3.5 ml of dehydrated methanol.

4. Add the solution prepared in step 2 to the solution prepared in step 3. It is important to maintain a 1 to 1 molar ratio of all-tans retinal to taurine.

5. To the reaction mixture prepared in Step 4, add 4.0 grams of molecular sieve having a size of 3 Angstroms, and stir the reaction mixture with a magnetic stirrer.

6. Maintain the reaction under continual stirring a) in the dark or under dim red light b) in the absence of oxygen c) in an atmosphere of argon d) at a temperature of −5 to −20 degrees Celsius.

7. Monitor the progression of the reaction until complete, by either thin layer chromatography (TLC) or High Pressure Liquid Chromatography (HPLC). Completion of the reaction will typically take approximately four (4) hours.

The reaction to form all-trans-retinyliden tauret may be monitored by TLC by periodic removal of aliquot samples of the reaction mixture and placing such reaction mixture on sheets of silica gel. The chromatograms may be developed with chloroform:methanol:trifluoroacetic acid in ratios of 20:6:1 or 10:1:0.1. The blots can then be visualized by spraying with sulfuric acid and heating, or by treatment with $I_2$ vapor.

The reaction to form all-trans-retinyliden tauret may be monitored by HPLC by placing 10 microliter samples of the reaction mixture on u-Bondapack $C_{18}$ columns for HPLC analysis. Methanol may be used as the mobile phase. The flow rate is preferably 1 ml/min. The absorbance is monitored at 360 nm.

It is recommended to run the synthesis in the presence of excess all-trans Retinal, because at the completion of the reaction it will be very easy to remove any excess all-trans tauret from the reaction container. All reaction solvents are removed by gentle heating of the reaction vessel and the application of gentle suction over any remaining liquids. Wash the precipitate with ether or hexane and filter the precipitate through a 16 cm glass filter connected to a vacuum line. Repeat the wash procedure two times. Dry the final precipitate under vacuum of 10 mmHg. The yield of this reaction is typically about 90%.

The all-trans isomer of retinyliden tauret (i.e., all-trans-3,7-dimethyl-9-(2,6,6-trimethyl-1-cyclohexen-1-yl)-2,4,6,8-nonatetraen-1-imido-(N-sulfonic acid) prepared in this example has the following characterization: a) Absorbency Max 365 um., b) Extinction Coefficient at 365 um is 40200, c) upon protonation the absorbency Max shifts to 444 um, d) the Extinction Coefficient at 444 um is 40050 e) Melting Point is 115 C., −116° C. and soluability in water is 200 mg/ml.

The all-trans isomer of retinyliden tauret synthesized by this method is stored under refrigeration at tempratures below −10 degrees Celsius, in amber glass bottles free of moisture and in an atmosphere free of oxygen. The compound should remain stored under such conditions until immediately before injection into the eye.

ii. A Preferred Synthesis for 11-cis-Retyliden Tauret

1. Dissolve 100 mg Taurine (i.e., 2-aminoethanesulfonic acid) in 5.0 ml of dehydrated methanol.

2. To the taurine/methanol solution prepared in step 1, add 2.0 ml of 0.8 N sodium methylate (i.e., sodium methoxide) in dehydrated methanol.

3. Dissolve 400 mg of all 11-cis-retinal (i.e., Vitamin A Aldehyde/Retinaldehyde or 11-cis-[3,7-dimethyl-9-(2,6,6-trimethyl-1-cyclohexen-1-yl)-2,4,6,8-nonatetraen-1-al]) in 3.5 ml of dehydrated methanol.

4. Add the solution prepared in step 2 to the solution prepared in step 3. It is important to maintain a 1 to 1 molar ratio of 11-cis-retinal to taurine.

5. To the reaction mixture prepared in Step 4, add 4.0 grams of molecular sieve having a size of 3 Angstroms, and stir the reaction mixture with a magnetic stirrer.

6. Maintain the reaction under continual stirring a) in the dark or under dim red light b) in the absence of oxygen c) in an atmosphere of argon d) at a temperature of −5 to −20 degrees Celsius.

7. Monitor the progression of the reaction until complete, by either thin layer chromatography (TLC) or High Pressure Liquid Chromatography (HPLC). Completion of the reaction will typically take approximately four (4) hours.

The reaction to form 11-cis-retinyliden tauret may be monitored by TLC by periodic removal of aliquot samples of the reaction mixture and placing such reaction mixture on sheets of silica gel. The chromatograms may be developed with chloroform:methanol:trifluoroacetic acid in ratios of 20:6:1 or 10:1:0.1. The blots can then be visualized by spraying with sulfuric acid and heating, or by treatment with $I_2$ vapor.

The reaction to form 11-cis-retinyliden tauret may be monitored by HPLC by placing 10 microliter samples of the reaction mixture on Separon SGX columns (7 um; 150×33 mm). The mobile phase is chloroform:methanol:trifluoroacetic acid in the ratio 87:13:0.1. 10 ul samples are injected and the flow rate is preferably 1.5 ml/min. The absorbance is monitored at 420 or 440 nm.

All reaction solvents are removed by gentle heating of the reaction vessel and the application of gentle suction over any remaining liquids. Wash the precipitate with ether or hexane and filter the precipitate through a 16 cm glass filter connected to a vacuum line. Repeat the wash procedure two times. Dry the final precipitate under vacuum of 10 mmHg. The yield of this reaction is typically above 90%.

The 11-cis isomer of retinyliden tauret synthesized by this method is stored under refrigeration at temperatures below −10 degrees Celsius, in amber glass bottles free of moisture and in an atmosphere free of oxygen. The compound should remain stored under such conditions until immediately before injection into the eye.

B. Formulations of Retinyliden Tauret for Injection or Topical Administration to the Eye The all-trans-retinyliden tauret and/or 11-cis-retinyliden tauret may be dissolved in an appropriate solvent to provide a solution for injection into the eye. However, such solution must be stored in the absence of light and under refrigeration at approximately 4 degrees C. and, even when stored under such conditions, its shelf life may be relatively short. One example of an appropriate retinyliden tauret solution for injection into the eye is as follows:

Liquid Solution for Injection

Retinyliden Tauret . . . 1–50 millimoles
Phosphate Buffer to pH 7.0 . . . 0.5–50 millimoles
Sterile Isotonic Saline Solution For Injection . . . 90–99% by weight As an alternative to manufacture and shipment of the above-described liquid solution for injection, and most preferably, the all-trans-retinyliden tauret and/or 11-cis-retinyliden, may be lyophilized immediately after synthesis and subsequently reconstituted immediately prior to injection into the eye. The lyophilized material must also be stored in the absense of light and under refrigeration at approximately –10 degrees C. until reconstitution and use. However, such lyophilized preparation may have a longer shelf life when stored under these conditions than the above-described liquid solution for injection. Four (4) examples of lyophilized formulations for the all-trans-retinyliden tauret and/or 11-cis-retinyliden tauret of this invention are as follows:

Lyophilized Preparation I

Retinyliden Tauret . . . 1 micromole–500 millimoles
Lactose . . . 2–50 mg
Phosphate Buffer to pH 6.5–7.4 . . . 0.1 micromoles–50 millimoles Lyophilized Preparation II Retinyliden Tauret . . . 1 micromole–500 millimoles
Sorbitol . . . 2–50 mg
Phosphate Buffer pH 6.5–7.4 . . . 0.1 micromoles–50 millimoles Lyophilized Preparation III Retinyliden Tauret . . . 100 millimoles
Lactose . . . 5 mg
Phosphate Buffer pH 7.0 . . . 0.2 millimoles Lyophilized Preparation IV Retinyliden Tauret . . . 100 millimoles
Sorbitol . . . 5 mg
Phosphate Buffer pH 7.0 . . . 0.2 millimoles At present, Lyophilized Preparation III is the preferred lyophilized formulation. It will be appreciated by those skilled in the art of formulation lyophilized pharmaceutical products that various other buffer systems, such as citrate or borate buffers, may be used in lieu of the phosphate buffer listed in the above examples.

The retinyliden tauret of the present invention may also be formulated for topical administration. The following is an example of a liquid solution of retinyliden tauret whish is suitable for topical administration:

Liquid Solution for Topical Administration or Retrobulbar Injection

Retinyliden Tauret . . . 1 micromole–500 millimoles
Phosphate Buffer pH 7.0 . . . 0.1 millimoles–10 milimoles
Polyethylene Glycol . . . 99% by weight The following is an example of a gel formulation which is also suitable for topical administration:

Gel Preparation for Topical Administration

Retinyliden Tauret . . . 1 micromole–500 millimoles
Phosphate Buffer pH 7.0 . . . 0.1 millimoles–10 milimoles
Hydroxypropyl Methyl Cellulose (2% aqueous solution) . . . 99% by weight At present, the above-set-forth formulation for the Gel Preparation for Topical Administration is the preferred gel formulation. However, it will be appreciated by those skilled in the art of formulating gel-type pharmaceutical products that various other cellulose materials or bulking agents, such as carboxymethylcellulose, may be used in lieu of the hydroxypropyl methyl cellulose component listed in the above example.

Additionally, the retinyliden tauret of this invention may be formulated in a lyposomal formulation for either topical application or retrobulbar injection, as described more fully under the heading "Methods and Routes of Administration for Treating Retinal Disorders with All-Trans-Retinyliden Tauret and/or 11-Cis-Retinyliden Tauret" herebelow. The following is an example of one such lyposomal formulation:

Lyposomal Formulation

Retinyliden Tauret . . . 1 micromole–500 millimoles
Phosphate Buffer pH 7.0 . . . 0.1 millimoles–10 milimoles
Lyposome . . . 99% by weight C. Methods and Routes of Administration for Treating Retinal Disorders with All-Trans-Retinyliden Tauret and/or 11-Cis-Retinyliden Tauret Solutions containing the all-trans-retinyliden tauret and/or 11-cis-retinyliden tauret of the present invention may be contacted with the retinal tissue of the eye to protect such retinal tissue from damage and/or to treat damage to or disoreders of the retina. Examples of retinal disorders which may be prevented, deterred, or treated by the administration of all-trans-retinyliden tauret and/or 11-cis-retinyliden tauret include, but are not necessarily limited to: retinitis pigmentosa, diabetic retinopathy, macular degeneration and other retinopathies of the mammalian eye.

The presently prefered dosage of all-trans-retinyliden tauret and/or 11-cis-retinyliden tauret for treating retinal disorders such as retinitis pigmentosa, is 1 micromole to 50 millimoles of tauret per administration, although any dose exhibiting suitable safety and nontoxicity may be used. The treatment may be delivered in a single dose or, if necessary, the treatment may be administered in repeat doses of 1 micromole–50 millimoles over a six (6) month period.

The preferred route of administration is intravitreal injection. However, it will be appreciated that other routes of administration may be used to deliver therapeutic amounts of the all-trans-retinyliden tauret and/or 11-cis-retinyliden tauret to the retina. Such other routes of administration may include topical administration upon the eye of a retinyliden tauret solution; topical administration upon the eye of a lyposomal preparation of retinyliden tauret; topical administration upon the eye of a gel preparation of retinyliden tauret; or retrobulbar injection of a solution or lyposomal preparation of retinyiden tauret.

To accomplish the treatment by intravitreal injection, the lyophilized product described hereabove as "Lyophilized Preparation 3" may be reconstituted in Sterile Isotonic Saline Solution for Injection U.S.P. to provide a solution having a retinyliden tauret concentration which allows the selected dose of retinyliden tauret (preferably between 1 micromole to 50 millimoles) to be injected directly into the vitreous in an injectate volume of 30–100 microliters, and preferably about 50 microliters. The patient's vision and clinical status may then be monitored, and and intravitreal injection may be repeated one or more times over a six (6) month period to arrest or deter the degeneration of the retina.

To accomplish the treatment by retrobulbar injection, one or more retrobulbar injection(s) will deliver sufficient amounts of retinyliden tauret, in a preparation or delivery system which will transport or distribute a therapeutic amount of the retinyliden tauret, to the retinal tissue. Such retrobulbar injections will preferably be carried out using a reconstituted lyophilized product such as that described hereabove as "Lyposomal Preparation 3", a liquid solution for injection such as that described hereabove as "Liquid Solution for Topical Administration or Retrobulbar Injection" or a lyposomal preparation such as that described hereabove as "Lyposomal Formulation."

To accomplish treatment by topical administration upon or around the eye, one or more topical application(s) will deliver sufficient amounts of retinyliden tauret, in a preparation or delivery system which will transport or distribute a therapeutic amount of the retinyliden tauret, to the retinal tissue. Such topical administration will preferably be carried out using; a gel form of the product such as that described hereabove as "Gel Preparation for Topical Administration", a liquid form of the product such as that described hereabove as "Liquid Solution for Topical Administration or Retrobulbar Injection" or a lyposomal form of the product such as that described hereabove as "Lyposomal Formulation."

The invention has been described hereabove with reference to certain presently prefered embodiments only, and no attempt has been made to exhaustively describe all possible embodiments of the invention. Indeed, various additions or modifications may be made to the particular embodiments described herein without departing from the intended spirit and scope of the invention. It is intended that all such additions and alterations to the above-described preferred embodiments be included within the scope of the following claims.

What is claimed is:

1. A method for treating a disorder of the retina of a mammalian eye, said method comprising the step of:
    A. contacting with the retina an effective amount of a compound having the formula 3,7-dimethyl-9-(2,6,6-trimehyl-1-cyclohexen-1-yl)-2,4,6,8-nonatetraen-1-imido-(N-ethane sulfonic acid).

2. The method of claim 1 wherein the compound contacted with the retina in step A comprises: all-trans-[3,7-dimethyl-9-(2,6,6-trimehyl-1-cyclohexen-1-yl)-2,4,6,8-nonatetraen-1-imido-(N-ethane sulfonic acid)].

3. The method of claim 1 wherein the compound contacted with the retina in step A comprises: 11-cis-[3,7-dimethyl-9-(2,6,6-trimehyl-1-cyclohexen-1-yl)-2,4,6,8-nonatetraen-1-imido-(N-ethane sulfonic acid)].

4. The method of claim 1 wherein a dose of 1 micromole-50 milimoles of said compound is contacted with the retina in Step A.

5. The method of claim 5 wherein Step A is repeated approximately 6 to 12 times at approximately monthly intervals.

6. The method of claim 1 wherein Step A is carried out by intravitreal injection of said compound.

7. The method of claim 1 wherein Step A is carried out by topical administration upon the eye of a solution containing said compound.

8. The method of claim 1 wherein Step A is carried out by topical administration upon the eye of a lyposomal preparation containing said compound.

9. The method of claim 1 wherein Step A is carried out by topical administration upon the eye of a gel preparation containing said compound.

10. The method of claim 1 wherein Step A is carried out by retrobulbar injection of a solution containing said compound.

11. The method of claim 1 wherein Step A is carried out by retrobulbar injection of a lyposomal preparation containing said compound.

12. A method of treating a disorder of the retina of a mammalian eye, said method comprising the step of:
    contacting with the retina a pharmaceutically acceptable preparation containing a retinyliden taurate compound in an amount that is effective to facilitate the transport of at least one retinoid between the pigment epithelium and the retina.

13. The method of claim 12 wherein the compound contacted with the retina in Step A has the formula 3,7-dimethyl-9-(2,6,6-trimehyl-1-cyclohexen-1-yl)-2,4,6,8-nonatetraen-1-imido-(N-ethane sulfonic acid).

14. The method of claim 13 wherein the compound contacted with the retina in Step A comprises: all-trans-[3,7-dimethyl-9-(2,6,6-trimehyl-1-cyclohexen-1-yl)-2,4,6,8-nonatetraen-1-imido-(N-ethane sulfonic acid)].

15. The method of claim 13 wherein the compound contacted with the retina in Step A comprises: 11-cis-[3,7-dimethyl-9-(2,6,6-trimehyl-1-cyclohexen-1-yl)-2,4,6,8-nonatetraen-1-imido-(N-ethane sulfonic acid)].

16. The method of claim 12 wherein Step A is repeated approximately 6 to 12 times at approximately monthly intervals.

17. The method of claim 12 wherein Step A is carried out by intravitreal injection of said compound.

18. The method of claim 12 wherein Step A is carried out by topical administration upon the eye of a solution containing said compound.

19. The method of claim 12 wherein Step A is carried out by topical administration upon the eye of a lyposomal preparation containing said compound.

20. The method of claim 12 wherein Step A is carried out by topical administration upon the eye of a gel preparation containing said compound.

21. The method of claim 12 wherein Step A is carried out by retrobulbar injection of a solution containing said compound.

22. The method of claim 12 wherein Step A is carried out by retrobulbar injection of a lyposomal preparation containing said compound.

* * * * *